United States Patent [19]

Kurbatov et al.

[11] Patent Number: 5,805,662
[45] Date of Patent: Sep. 8, 1998

[54] USING DEFLECTED PENETRATING RADIATION TO IMAGE AN OBJECT'S INTERNAL STRUCTURE

[75] Inventors: Alexey V. Kurbatov, Moscow, Russian Federation; Pavel I. Lazarev, Menlo Park, Calif.

[73] Assignee: Quanta Vision, Inc., Santa Clara County, Calif.

[21] Appl. No.: 569,031

[22] Filed: Dec. 7, 1995

[30] Foreign Application Priority Data

Dec. 8, 1994 [RU] Russian Federation ............. 94043357

[51] Int. Cl.$^6$ .................................................. G01N 23/201
[52] U.S. Cl. ................................ 378/87; 378/86; 378/57; 378/154
[58] Field of Search ...................... 378/7, 84, 85, 378/86, 87, 89, 90, 145, 147, 148, 57, 154

[56] References Cited

U.S. PATENT DOCUMENTS

| 4,075,492 | 2/1978 | Boyd et al. ................................. 378/7 |
| 5,319,694 | 6/1994 | Ingal et al. ................................. 378/84 |

FOREIGN PATENT DOCUMENTS

| PM0583 | 8/1993 | Australia . |
| PM1519 | 9/1993 | Australia . |
| PM1597 | 10/1993 | Australia . |
| PM4298 | 3/1994 | Australia . |
| WO/95/05725 | 2/1995 | WIPO . |

OTHER PUBLICATIONS

L. M. Soroko, "Gilbert's Optics," Nauker, 1981, pp. 34–37, 90–93, 126–127, 160–169, and 236–239.

Vinogradov et al., "Investigation of a Steering Mirror for the Soft X–Ray Region," Nuclear Instruments and Methods in Physics Research, 1987, pp. 11–12.

Vinogradov et al., "Turning a Ray of Soft X–Ray Radiation by Means of a Spherical Surface," (Russian publication, 13 Nov. 1985) pp. 594–596.

Mitrofanov, et al, Method of Obtaining the Shadow of an Object Internal Structure with the aid of Penetrating Radiation, *NAOUKA* Pub., 1982, pp. 221–222.

*Primary Examiner*—Don Wong
*Attorney, Agent, or Firm*—Skjerven, Morrill, MacPherson, Franklin & Friel; David T. Millers

[57] ABSTRACT

A method of nondestructive investigation of the internal structure of an object uses deflected penetrating radiation. In one embodiment, an incident penetrating radiation flow 4 with angular divergence restricted by a collimator 3 passes through an object 5 to create the a radiation flow 6 registered by a direction-selective detector 10. Typically, the directivity pattern of detector 10 selects a desired angle and has a width no larger than twice the local angular divergence of the incident penetrating radiation flow 4. The desired angle can be the maxima of a scattering pattern for a substance suspected of being in object 5. To improve the quality and range of measurements, the local restrictions of radiation flow 4 is fulfilled in the two intersecting planes; and detector 10 and/or incident radiation flow 4 can be swept through a range of orientations to detect radiation deflected at a range of angles larger than the directivity pattern detector 10 has when fixed.

17 Claims, 6 Drawing Sheets

USING DEFLECTED PENETRATING RADIATION TO IMAGE AN OBJECT'S INTERNAL STRUCTURE

BACKGROUND OF THE INVENTION

1. Field of the Invention

This invention relates to systems and methods for using penetrating radiation, and in particular for using radiation deflected in an object, to image the internal structure of an object.

2. Description of Related Art

Irradiating an object with penetrating radiation such as X-rays and then measuring the spatial intensity distribution of radiation which exits the object provides an image (or more accurately a projection) of the internal structure of the object. Photographic film sensitive to the radiation can record or register the radiation intensity and capture the image. On the film, the object is represented as areas having different degrees of exposure. Light areas represent parts of the object that attenuate the penetrating radiation, and dark areas represent parts of the object that are more penetrable to the radiation. Soft tissues of plants or animal are difficult to analyze using intensity attenuation of hard radiation because soft tissues only slightly attenuate hard radiation and images indicating a pattern of attenuation tend to have low contrast.

Imaging methods which use low dosage of hard radiation and provide high contrast images of soft tissue are desired for the medical investigation of biological objects. One technique for improving contrast removes background radiation at refractive angles and is described in certificate USSR #1402871 (priority date Nov. 13, 1986). The method includes a first collimation of the penetrating radiation flow propagating from a source to provide a narrow angular range for radiation incident on an investigated object. The flow passes through the investigated object, and a second collimation isolates a portion of the flow which has a small angular divergence from the original direction of the flow. The second collimator directs that portion to a detector which forms an image and blocks a deflected portion of the radiation flow that passes through the object and is spread outside the angular range of the second collimator. Eliminating the spread out radiation provides more contrast in the image than appears in a common roentgenogram.

It was later suggested that the angular divergence of the incident radiation flow be at least half as large as the corresponding angular interval of the radiation flow that has been passed through the second collimator (see, for example, USSR Patent #4934958 or related U.S. Pat. No. 5,319,694). This method intensifies contrast in images of objects including objects with low attenuating ability, composed of areas that differ in ability to scatter the penetrating radiation.

SUMMARY OF THE INVENTION

In accordance with the invention, improved contrast in an image is obtained using penetrating radiation deflected in the process of propagation through an object. Many objects that do not contain significant variations in absorption characteristics for a given type of radiation do contain significant variation in scattering properties, especially for small-angle scattering. For example, such objects as living organisms often contain tissues that are highly ordered and produce distinctive small-angle scattering and diffraction patterns, and specific x-ray diffraction patterns for tissues such as muscle, cartilage, mucus, and lipids are known. This knowledge allows enhancement of contrast in images by selecting radiation deflected at an angle distinctive of a particular component of an object being imaged. Improved contrast imaging of an object's internal structure can be accomplished by registration of the radiation selected according to the scattering and refractive properties of the object being imaged.

In accordance with one embodiment of the invention, the local divergence angle of an incident penetrating radiation flow is restricted, then this flow is passed through an investigated object and registered by the direction-selective detector to form an image. Typically, the incident penetrating radiation flow is shaped in so that its angular divergence is no less than one half of the width of the detector's directivity pattern. In particular, the angular divergence of the incident penetrating radiation flow is equal to or exceeds half of the width of the detector's directivity pattern in the plane of the minimal radiation divergence. Having a smaller angular divergence decreases flux without providing a corresponding improvement in the ability to detect deflections.

Restriction of the angular divergence of incident penetrating radiation can be independently applied in two intersecting planes. In this case, the ratio of the angular divergence measured in one plane to the angular divergence measured in the other plane should be no less than about 1:10. Otherwise, the high angular divergence in one plane diminishes the overall angular sensitivity. Restriction of the angular divergence of the incident radiation relative to a plane may be carried out with crystals having scattering surfaces that form interference reflections at an angle characteristic of the crystal and the wavelength of the penetrating radiation. Alternatively, a set of closely spaced plates opaque to the penetrating radiation can absorb radiation that strikes the plates and restrict angular divergence perpendicular to the plates.

A direction-selective detector having a directivity pattern shaped in the two intersecting planes can select radiation deflected at desired angles. The selected radiation is used to form the image.

In one embodiment of the invention, the relative orientation of direction-selective detector and the primary axis of the incident penetrating radiation moves across a range. This expands the angular range of deflected radiation that is detected by the direction-selective detector. Changing the relative orientation of detector and incident radiation also allows independent measurements of intensities at different deflection angles and allows detection of distinctive scattering and diffraction patterns indicating the presence and position of particular materials.

In one embodiment, a direction-selective detector has a digital output for a computer or specialize circuitry which processes data. A processing procedure executed by the computer can compute contrast and define more precisely the genesis of detected radiation using measured angles and stored reference data concerning the angular scattering characteristics of substances which may be present in the investigated object. In combining measurements from different relative orientations of the direction-selective detector and incident radiation, the processing procedure can detect correlations between measured two-dimensional radiation intensity distributions at the different orientations and compensate for shifts in the image caused by movement of the detector or incident radiation.

BRIEF DESCRIPTION OF THE DRAWINGS

Use of the same reference symbols in different figures indicates similar or identical items.

DETAILED DESCRIPTION OF THE PREFERRED EMBODIMENTS

Figure 1:
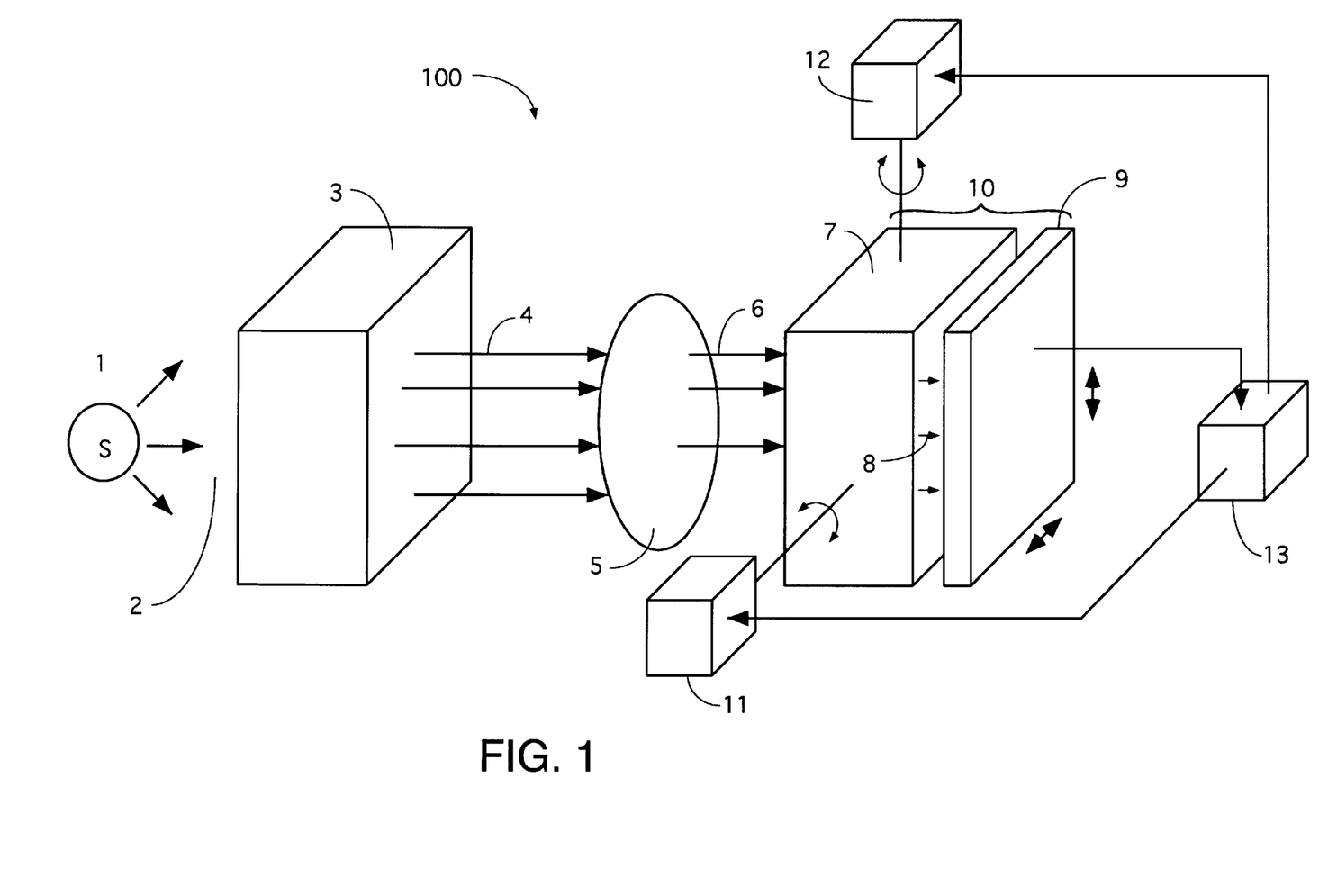
FIG. 1 shows an imaging system in accordance with an embodiment of the invention.

FIG. 1 shows a system 100 for imaging an object 5 using penetrating radiation. A source 1, which may be a Roentgen tube, generates a penetrating radiation flow 2. A collimator 3 placed in radiation flow 2 restricts local angular divergences of radiation flow 2 to produce a radiation flow 4. Collimator 3 directs radiation flow 4 to object 5 and restricts angular divergence at each point in radiation flow 4. Radiation flow 4 is sometimes referred to herein as the incident radiation because radiation flow 4 is incident on the investigated object 5.

Radiation flow 4 interacts with the substance of object 5 during the propagation through object 5. The interactions include absorption, refraction, diffraction, and scattering. Radiation flow 6 exits object 5 after undergoing the interactions with object 5 and passes through a collimator 7 which isolates a radiation flow 8 from flow 6. A detector 9 measures a two-dimensional spatial intensity distribution of radiation in flow 8 which forms a projection of object 5.

Detector 9 together with collimator 7 constitute a direction-selective detector 10. Direction-selective detector 10 detects radiation having directions of propagation that are selected by the orientation of direction-selective detector 10 and a directivity pattern characteristic of detector 10. In the embodiment shown, direction-selective detector 10 has drives 11 and 12 which can change the orientation of detector 10 relative to the direction of incident radiation flow 4. Control circuitry 13, which may be a general purpose computer or specialized circuitry, controls drives 11 and 12 and obtains information from detector 9 to, for example, automatically process the information and improve the contrast in an image.

Figure 2A:
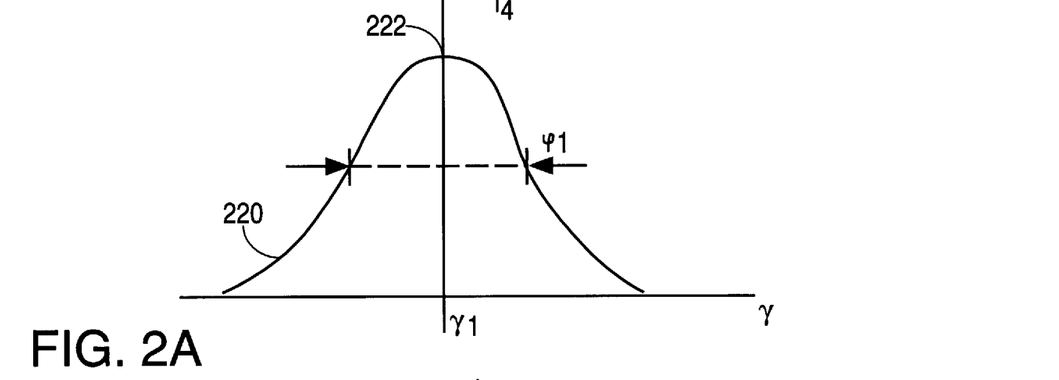
FIGS. 2A, 2B, 2C, and 2D illustrate a process of forming an incident penetrating radiation flow and measuring deflected radiation.

The incident radiation flow 4 has a restricted angular divergence so that an angular distribution of radiation flow 4 has a sharply defined maximum intensity along an axis of propagation for radiation flow 4. FIG. 2A shows an angular distribution I4 of radiation intensity for a projection of radiation flow 4 onto a plane. Angular distribution I4 has a maximum at an angle γ1 which represents the direction of the axis projected into the plane. The full width at half maximum (FWHM) of angular distribution I4 is an angular interval φ1 which gives a measure of the angular divergence of radiation flow 4 from the axis. The FWHM is defined so that inside the interval φ1 around maximum 222 the intensity at each angle is no less than half of maximum 222.

Figure 2B:
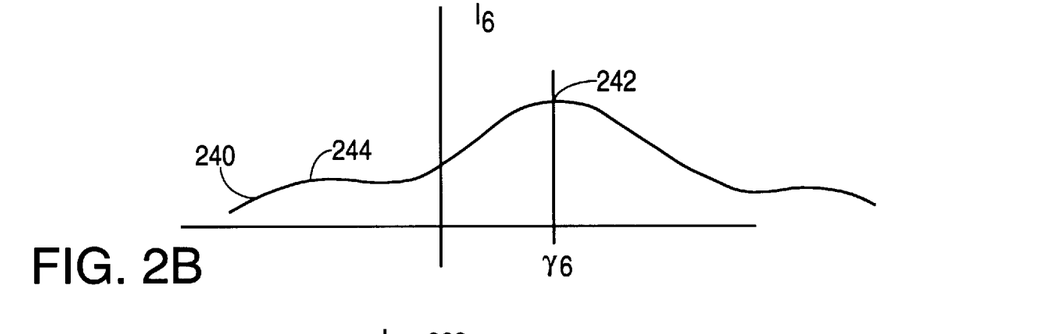

Radiation flow 4 can be refracted, diffracted, scatter, and absorbed during propagation through investigated object 5 before radiation flow 6 exits object 5. FIG. 2B shows an example a profile of an angular distribution of intensity I6 at a selected point in radiation flow 6. As a result of refraction in object 5, profile IG has a maximum 242 at an angle γ6 that is displaced relative to the direction γ1 that radiation flow 4 has before entering investigated object 5. Maximum 242 of intensity profile I6 is lower than the maximum of intensity profile I4 because of absorption and scattering in object 5. Profile I6 has secondary maxima 244 which indicates that low-angle scattering may be caused by diffraction in an ordered structure inside investigated object 5.

Refraction of radiation in general and of X-rays in particular is determined primarily by changes in the density in an object and is mostly independent of the elements which constitute the object. The fine physical structure (molecular packing, presents of colloidal particles, microphores and so on) in investigated object 5 controls the nature of X-ray scattering. Accordingly, scattered radiation can provide information about more than the density distribution inside object 5. Such information indicates the positions of substances in object 5 that have identifiable small angle diffraction and scattering patterns.

Figure 2C:
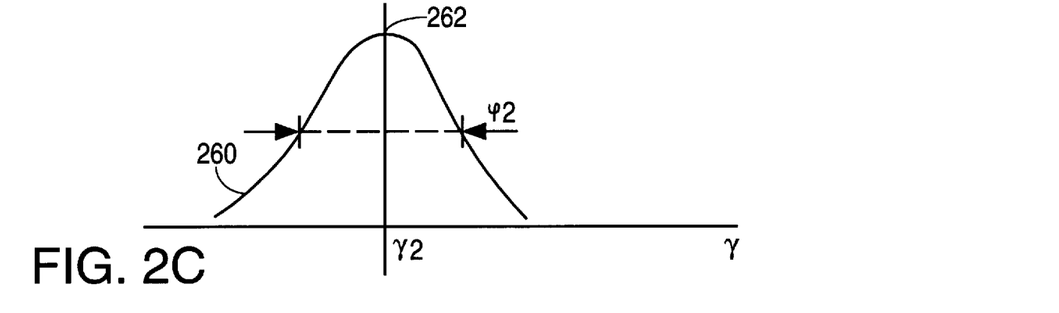

In direction-selective detector 10, collimator 7 selects from incident radiation 6 output radiation 8 which is propagating in a direction corresponding to the orientation of collimator 7; and detector 9 detects the radiation selected by collimator 7. FIG. 2C shows a directivity pattern 260 representing the angular selectivity of collimator 7 and therefore of direction-selective detector 10. Pattern 260 shows the existence of maximal detection efficiency for a direction γ2. In the vicinity of direction γ2, the efficiency of detector 10 decreases. The full width at half maximum φ2 indicates the width of directivity pattern 260. The transmittance of collimator 7 for radiation within the angular range φ2 is no less than one half of the maximum transmittance.

Figure 2D:
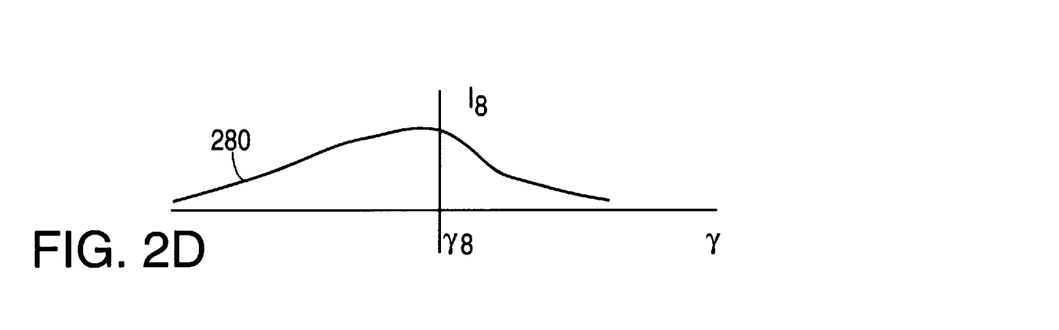

Detector 9 registers penetrating radiation flow 8 as a two-dimensional spatial distribution of intensity which provides a projection of object 5. Each point of detector 9 detects radiation corresponding to a point in the projection and accepts radiation propagating in all directions through the point. However, collimator 7 has restricted the local angular divergence according to the directivity pattern 260. FIG. 2D shows a curve 280 characterizing a local angular distribution of intensity I8 of radiation flow 8 at a point in the projection.

To optimize registration of scattering effects caused by propagation through investigated object 5, radiation flow 4 has a minimal angular divergence projection that is equal to the width of the directivity pattern of detector 10. As noted above, radiation flow 4 has restricted angular divergence φ1 that is equal to width φ2 of directivity pattern 260.

Figure 3:
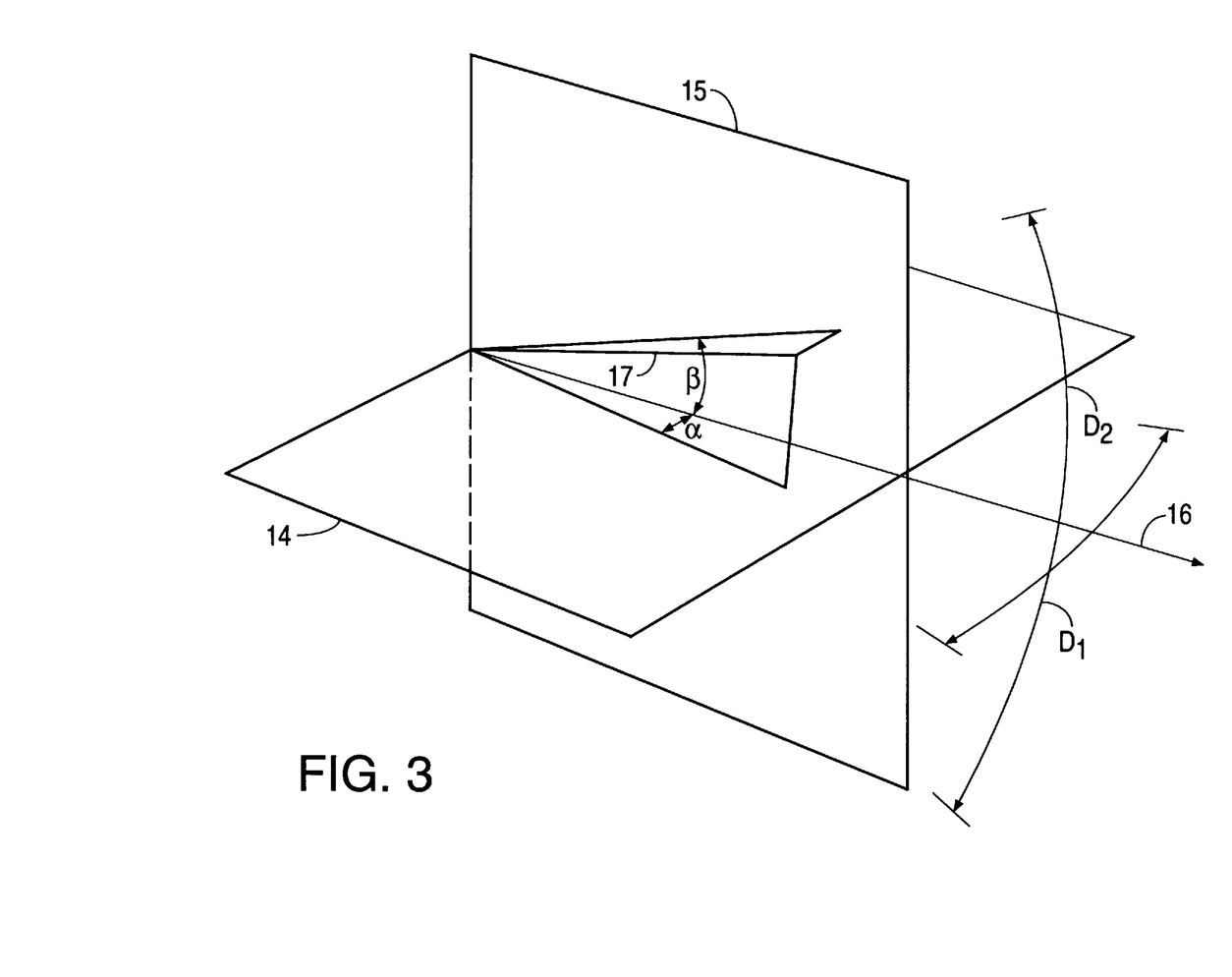
FIG. 3 illustrates parameters describing a penetrating radiation flow when angular divergence is restricted in two intersecting planes.

To reduce background noise caused by radiation which enters and exits object 5 at large angles, the restriction of the angular divergence of radiation flow 4 can be in two perpendicular planes. FIG. 3 shows two perpendicular planes 14 and 15 intersecting along an axis 16 which is the direction of maximal intensity in radiation flow 4. A ray 17 propagating along a direction that differs from axis 16 can be characterized by two angles α and β between axis 16 and projections of ray 17 on planes 14 and 15. The intensity of radiation flow 4 decreases with increasing angles α and β in a manner that depends on intensity profiles for planes 14 and 15. An angle D1, which is referred to herein as the local angle of divergence in plane 14, is the angle at which the total intensity of rays 17 having angle α equal to D1 is half the total intensity of rays having angle α equal to zero. Similarly, an angle D2, which is referred to herein as the local angle of divergence in plane 15, is the angle at which the total intensity of rays 17 having angle β equal to D2 is half the total intensity of rays having angle β equal to zero.

Restriction of radiation flow 4 by two angles of local divergence D1 and D2 in planes 14 and 15 improves angular resolution and facilitates the task of obtaining more detailed information about the internal structure of object 5. In a process which only restricts divergence in one plane, the divergence in another plane may be large in comparison with the restricted divergence. This makes selection of a desired refraction, scattering, or diffraction angle for measurement difficult because the large divergence creates a background of radiation having different deflections but exiting object 5 along the same direction. A specific embodiment of the invention restricts divergence angles D1 and D2 so that the ratio of the larger divergence angle to the smaller divergence angle does not exceed 10.

Figure 4A:
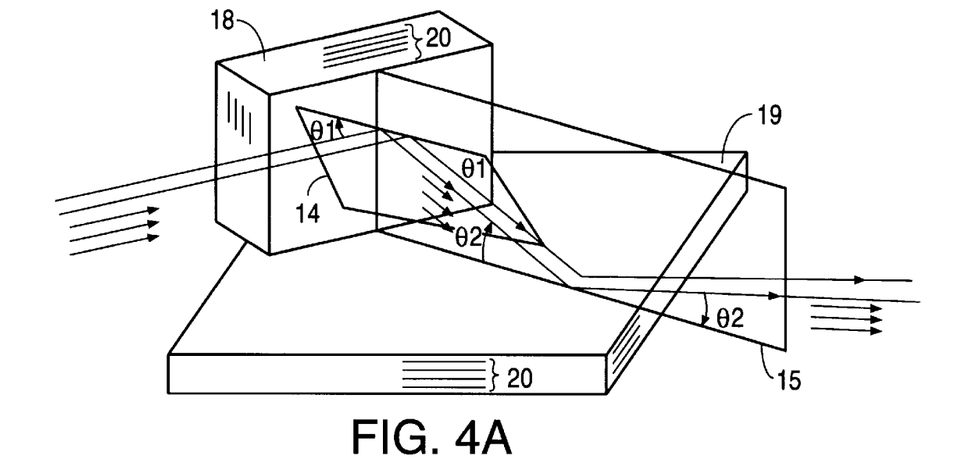
FIGS. 4A and 4B illustrate methods for restricting angular divergence using systems of scattering or reflecting surfaces.

Many different types of collimators can be used to restrict of angular divergences in radiation flows 4 and 8. In particular, FIG. 4A shows a collimator containing elements 18 and 19 which are crystals or multilayer interference mirrors having a plurality of regularly located scattering surfaces 20. Scattering surfaces 20 create interference reflections which have high angular selectivity. An incoming penetrating radiation flow reflects most efficiently from elements 18 or 19 when the incidence angle θ or θ2 satisfies Bragg's equation for the respective element 18 or 19. Small angular deviations from Bragg's angle cause substantial weakening of the interference reflection.

To restrict divergence of the radiation flow relative to two perpendicular planes 14 and 15, elements 18 and 19 are positioned so that scattering surfaces 20 in element 18 are perpendicular to scattering surfaces 20 in element 19. Incoming radiation at Bragg's angle θ1 for element 18 reflects from element 18. This restricts angular divergence in plane 14 which contains the incident and reflected rays for element 18. Radiation reflected from element 18 strikes element 19, and only those rays at an angle approximately equal to Bragg's angle θ2 for element 19 are reflected from element 19. Accordingly, element 19 restricts angular divergence relative to a plane containing a ray reflected from element 18 and the resulting ray reflected from element 19. The double interference reflections produced by surfaces 20 of elements 18 and 19 create a radiation flow with restricted local angular divergence in two intersecting planes 14 and 15.

Figure 4B:
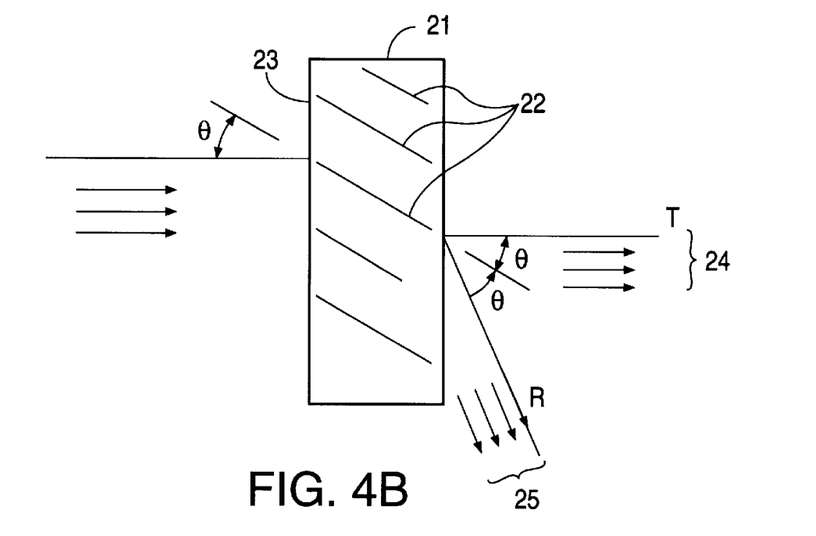

Another process uses Bormann's effect to restrict angular divergence radiation flow. Bormann's effect appears when the radiation flow is directed at an element 21 which is a thick crystal or interference structure having interference planes 22 at a substantial angle with an outer face 23 of element 21. The radiation incident on element 21 at Bragg's angle relative to planes 22 emerges from element 21 as rays 24 and 25 after being subjected to interference reflection and transmission at interference planes 22. Element 21 attenuates the fraction of the radiation flow at angles different from Bragg's angle. Accordingly, element 21 acts as the direction-selective element in regard to incident radiation and can be used in place of element 18 or 19 in the collimator of FIG. 4A.

Figure 5:
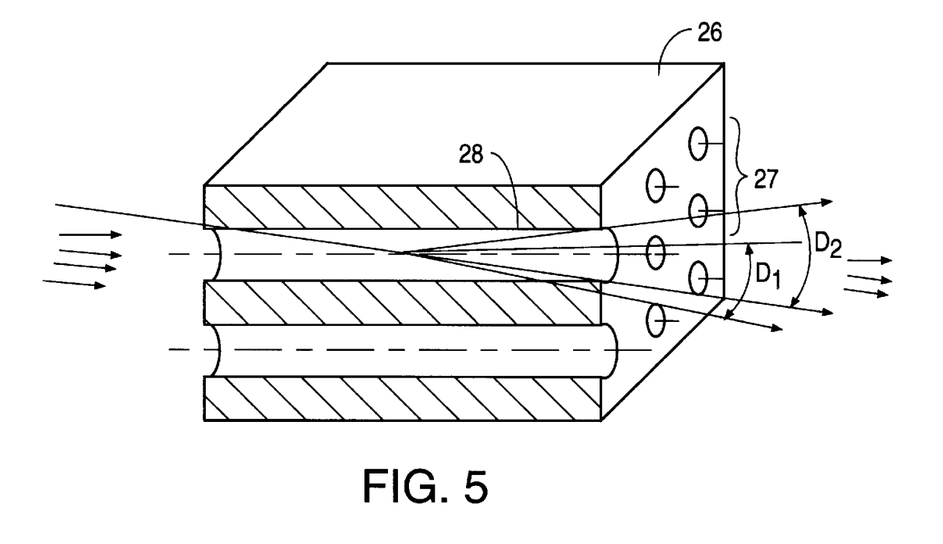
FIG. 5 shows a collimator which restricts angular divergence using of mechanical stop down.

FIG. 5 shows an embodiment of the invention which uses a mechanical stop as a collimator to restrict local angular divergence of flows 2 or 6 in two intersecting planes. The mechanical stop consists of a block 26 having a plurality of parallel spaced tubular channels 27 having a length many times greater than their diameter. Local angular divergence angles D1 and D2 of the output radiation flow depend on the ratio of the widths in each plane 14 and 15 to the length of propagation inside a channel 27 before reflection from a surface 28 of the channel 27. The maximal restriction of angular divergence is attained in the absence of the radiation reflection from surfaces 28 of channels 27.

Block 26 can be used as collimators 3 and 7 shown on FIG. 1. Alternatively, several blocks 26 placed sequentially along the axis of the radiation flow propagation can be used. A sequence of several blocks 26 with a gradual increase of the channels' cross-section from one block to another maximizes the transmission of the penetrating radiation flow to detector 9 and reduces the fraction of the penetrating radiation flow attenuated by channel surface 28 of tube element 27.

Microlenses (not shown) can be built in the orifices of channel elements 27 to decrease the fraction of the penetrating radiation that is blocked or scattered at the orifices of channel elements 27. Microlenses can be formed using drops of glass, paraffin, or other materials in the orifices to form converging lenses having long focal lengths.

Figure 6:
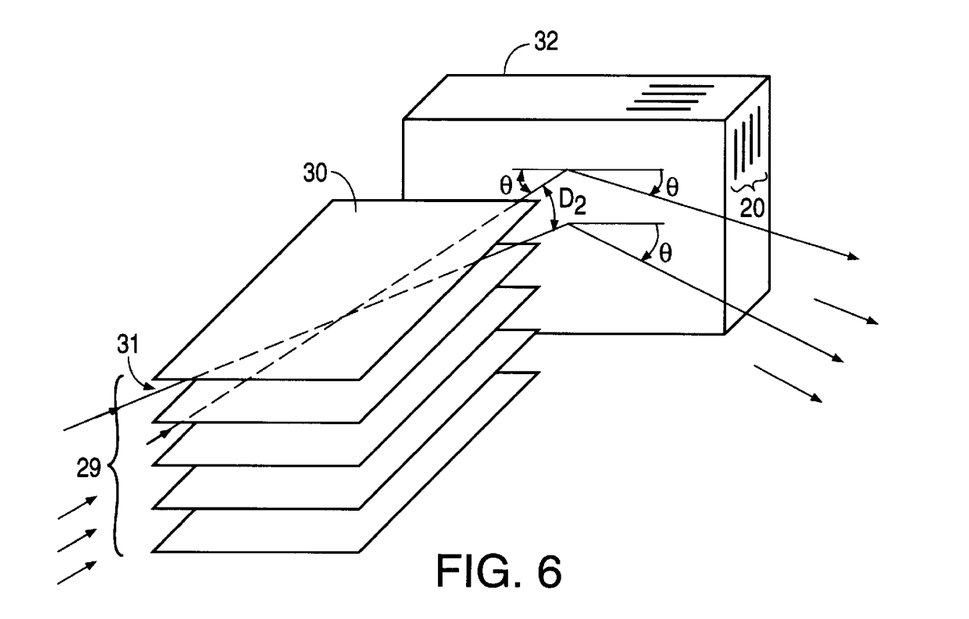
FIG. 6 shows a collimator which restricts angular divergence using a mechanical stop down and a system of scattering surfaces that produce an interference reflection.

FIG. 6 shows an embodiment of the invention wherein a collimator 29 includes closely spaced plates 30 made from materials opaque to incident penetrating radiation. Plates 30 restrict the local angular divergence of radiation 2 and 6 in a first plane perpendicular to plates 30. The magnitude of the local angular divergence perpendicular to plates 30 is determined by the ratio of the distance between two neighboring plates 30 to the length of a gap 31 along the direction of radiation flow.

A second element 32 restricts the local angular divergence in the second plane. In FIG. 6, element 32 is a crystal having scattering planes 20 at the Bragg's angle with resect to the desired incident and reflected radiation. In alternative embodiment, another apparatus for restricting angular divergence in the second plane can be used.

Figure 7A:
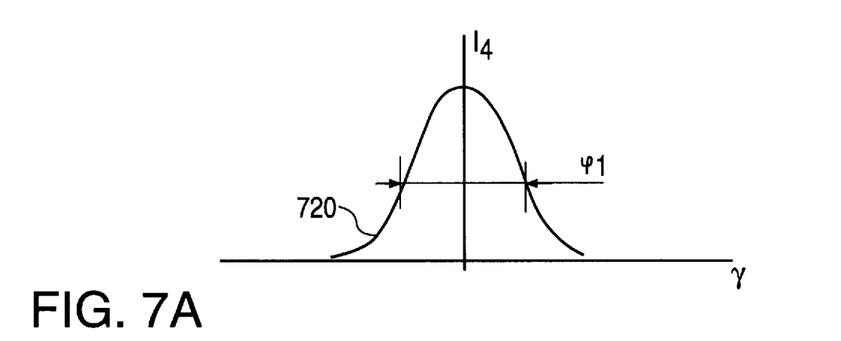
FIGS. 7A, 7B, 7C, and 7D illustrate an imaging process which sweeps the orientation of the penetrating radiation flow relative to a direction-selective detector.
Figure 7B:
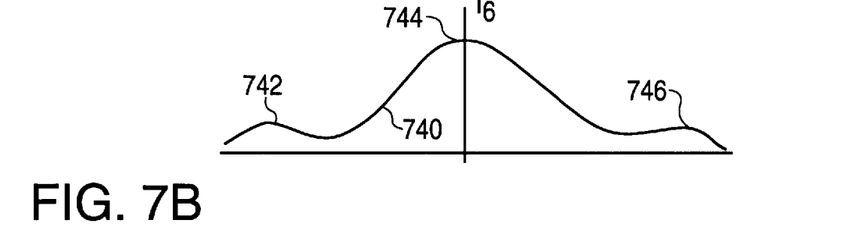

To obtain more information about the distribution of the substances causing scattering in object 5, direction-selective detector 10 and radiation flow 4 are rotated relative to each other. For example, radiation flow 4 stays stationary while drives 11 and 12 rotate detector 10 about two perpendicular axis. FIGS. 7A, 7B, 7C, and 7D illustrate an imaging method where the relative orientation of collimator 3 and detector 10 change during investigation of the structure of object 5. FIG. 7A shows a curve 720 characterizing a local angular intensity distribution I4 in radiation flow 4. Curve 740 shown in FIG. 7B represents a local angular intensity distribution I6 in radiation flow 6 exiting object 5. Many substances such as polycrystalline metals, polymers, gravels, and tissues of plants and animals have diffraction patterns with small-angle scattering at specific maxima such as maxima 742, 744, and 746 shown on FIG. 7B. The present method can select angles for forming a contrast image of the internal structure of object 5. In particular, an angle corresponding to a diffraction maxima of a substance can be use to infer the location of that substance in object 5. Human or animal muscle, for example, have different position of diffraction pattern maxima for contracted and relaxed states, and the position of contracted and relaxed muscle can be identified using radiation deflected into angles corresponding to their respective diffraction maxima.

Figure 7C:
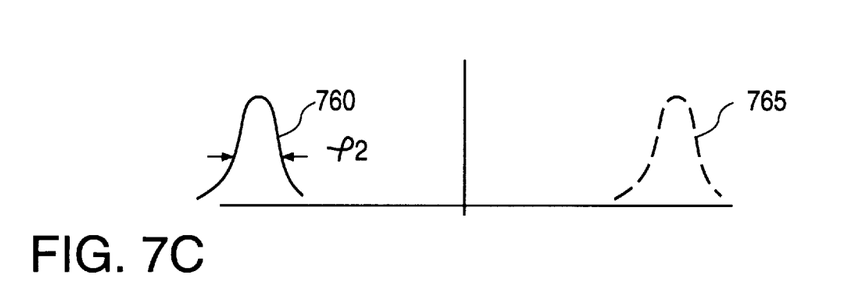

FIG. 7C shows two directivity patterns 760 and 765 corresponding to two orientations of direction-selective detector 10. These orientations were chosen for the selective registration of the first order maxima 742 and 746 of angular intensity distribution 740. Detector 10, in the process of registering the internal structure of object 5, can swing from the orientation corresponding to directivity pattern 760 to the orientation corresponding to directivity pattern 765 to detect radiation from both first order maxima 742 and 746. The patterns and maximums being specific can indicate the presence and location of certain substances in object 5.

Figure 7D:
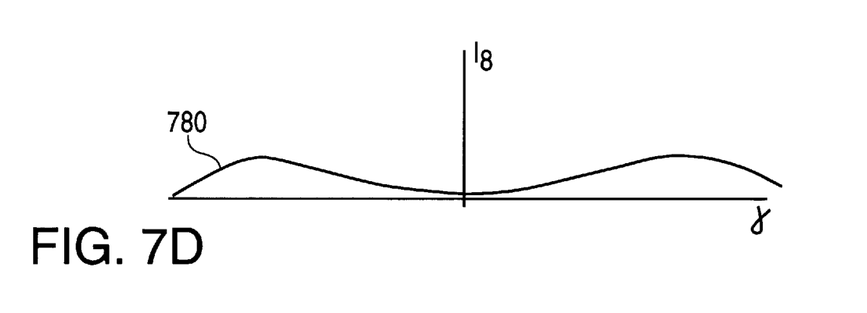

A curve 780 (FIG. 7D) shows a local angular intensity distribution I8 of radiation flow 8 which has passed through collimator 7 and is directed to a specific area of position-sensitive detector 9 which is intended to register the two-dimensional distribution of the radiation intensity. The intensity of radiation reaching detector 9 is greatest in areas which correspond to portions of object 5 which contain substances that tend to scatter radiation at the angles selected by directivity patterns 760 and 765.

Changing the relative orientation of detector 9 and radiation flow 4 can displace the projection of a structure in object 5 on detector 9. Digital processing of an electric signal output from detector 9 to computer 13 can compensate for the displacement by moving detector 9 linearly. In one embodiment of the invention detector 9 is camera that produces the digital output for computer 13. Such digital output contains portions which correspond to elements for spatial resolution in detector 9 and a set of different relative orientations of radiation flow 4 and detector 10. In processing data from detector 9, computer 13 can use stored information about the scattering (or diffraction) patterns that are specific to substances supposedly composing object 5.

The selectivity of detector 10 to the scattered radiation flow 6 after it has passed through investigated object 5 is effectively changed by angular motion or rocking of detector 10 through a user selected range relative to radiation flow 4. Variable speed over the range of motion can emphasize sensitivity to particular angles relative to others. For example, the steady swinging of the direction-selective detector 10 during the exposure time extends the directivity pattern of detector 10 to include a range of angles in the plane of swinging where all angles in the range are equally weighted. Accordingly, a detector having a collimator 7 which includes a crystal having a selectivity to a few arc seconds can be swung over a range of orientation to provide selective registration of angular scattering characteristics in a wide region. Alternative methods for object imaging swing or sweep radiation flow 4 and/or detector 10 using digitally controlled drives (not shown) attached to collimator 3 and/or 7.

Although the present invention has been described with reference to particular embodiments, the description is only an example of the invention's application and should not be taken as a limitation. Various adaptations and combinations of features of the embodiments disclosed are within the scope of the present invention as defined by the following claims.

We claim:

1. A method for investigating the internal structure of an object, the method comprising:

restricting an angular divergence of a beam of penetrating radiation which has a maximum intensity propagating along a first axis, wherein restricting the angular divergence comprises restricting the beam so that the beam has a maximum local angle of divergence in a first plane and a minimum local angle of divergence in a second plane and the maximum local angle of divergence is less than 10 times the minimum local angle of divergence;

transmitting the beam through the object; and using a direction-selective detector to register a portion of the radiation which exits the object, wherein the direction-selective detector has a directivity pattern centered along a second axis that is at a non-zero angle with an undeflected path of the beam, the directivity pattern having a width that does not exceed twice the minimum local angle of divergence.

2. The method of claim 1, wherein the maximum local angular divergence that is greater than half of the width of the detector's directivity pattern.

3. The method of claim 2, wherein the minimum local angle of divergence of the beam is equal to the width of the detector's directivity pattern.

4. The method of claim 1, wherein restricting the beam further comprises:

directing penetrating radiation at a first element which limits the angular divergence in one of the first and second planes; and directing penetrating radiation from the first element to a second element which restricts the angular divergence of in the other of the first and second planes.

5. The method of claim 4, wherein directing penetrating radiation at the first element comprises directing radiation at scattering surfaces that create an interference pattern with a maxima within a restricted angular range.

6. The method of claim 4, wherein directing penetrating radiation at the first element comprises directing radiation at a set of parallel plates which are opaque to the penetrating radiation.

7. The method of claim 1, further comprising:

sweeping the first axis relative to the direction-selective detector to vary the angle between the first axis and the second axis;

using the direction-selective detector to register a portion of the radiation which exits the object at a least two relative orientations within the range; and combining results of registering radiation in different orientations to form an image.

8. The method of claim 7, further comprising moving the direction-selective detector to compensate for the sweeping causing for movement of a projection of the object.

9. The method of claim 7, wherein using the direction-selective detector further comprises generating a digital signal indicating intensity of penetrating radiation registered by the direction selective detector, and using a computing procedure to process separate measurements registered at different relative orientations of the first axis and the second axis.

10. The method of claim 9, wherein using the computing procedure comprises comparing measurements to stored data which represent an angular distribution for a known substance.

11. An imaging system comprising:

a source of penetrating radiation;

a collimator positioned relative to the source of penetrating radiation so as to produce a collimated beam of penetrating radiation which is centered along a first axis and transmitted into a region for containing an object to be imaged, the collimator comprising:

a first element which limits the angular deviation of penetrating radiation in a first plane; and a second element which limits the angular deviation of penetrating radiation in a second plane; and a direction-selective detector positioned to receive radiation from the collimator which passes through the object region, the direction-selective detector having a directivity pattern centered along a second axis that is at a non-zero angle with an undeflected path of the collimated beam.

12. The imaging system of claim 11, wherein the first element comprises a first crystal, and the second element comprises a second crystal.

13. The imaging system of claim 11, wherein the first element comprises a mechanical stop which limits angular deviation in the first plane, and the second element comprises a crystal oriented to limit angular deviations in the second plane.

14. The imaging system of claim 11, further comprising a drive system which changes an orientation of the direction-selective detector relative to the collimator.

15. An imaging system comprising:

a source of penetrating radiation;

a collimator positioned relative to the source of penetrating radiation so as to produce a collimated beam of penetrating radiation that has an angular distribution centered about a first axis and is transmitted into a region for containing an object to be imaged, wherein the collimated beam has a maximum local angle of divergence in a first plane and a minimum local angle of divergence in a second plane, and the maximum local angle of divergence is less than 10 times the minimum local angle of divergence;

a direction-selective detector positioned to receive radiation from the collimator which passes through the object region, the direction-selective detector having a directivity pattern centered about a second axis; and a drive system which changes an orientation of the direction-selective detector relative to the collimator to vary an angle between the first and second axes.

16. The imaging system of claim 15, wherein the drive system is coupled to the direction-selective detector and rotates the direction-selective detector relative to the collimator.

17. The imaging system of claim 15, wherein the drive system is coupled to the collimator and rotates the collimator relative to the direction selective detector.

* * * * *